United States Patent
Xu

(10) Patent No.: US 10,525,246 B2
(45) Date of Patent: Jan. 7, 2020

(54) MICRODEVICE AND METHOD FOR TRANSDERMAL DELIVERY AND SAMPLING OF ACTIVE SUBSTANCES

(71) Applicant: NANOMED SKINCARE, INC., Cupertino, CA (US)

(72) Inventor: Bai Xu, Cupertino, CA (US)

(73) Assignee: NANOMED SKINCARE, INC., Cupertino, CA (US)

(*) Notice: Subject to any disclaimer, the term of this patent is extended or adjusted under 35 U.S.C. 154(b) by 0 days.

(21) Appl. No.: 15/714,628

(22) Filed: Sep. 25, 2017

(65) Prior Publication Data
US 2018/0021559 A1    Jan. 25, 2018

Related U.S. Application Data

(63) Continuation-in-part of application No. 11/961,816, filed on Dec. 20, 2007, now abandoned.
(Continued)

(51) Int. Cl.
*A61M 37/00* (2006.01)
*A61K 9/00* (2006.01)
(Continued)

(52) U.S. Cl.
CPC ....... *A61M 37/0092* (2013.01); *A61K 9/0014* (2013.01); *A61K 9/0021* (2013.01); *A61K 9/127* (2013.01); *A61K 9/7007* (2013.01); *A61K 9/7023* (2013.01); *A61K 31/167* (2013.01); *A61K 31/245* (2013.01); *A61K 31/337* (2013.01); *A61K 38/21* (2013.01); *A61M 37/0015* (2013.01); *A61N 1/303* (2013.01); *A61P 35/00* (2018.01); *A61M 2037/003* (2013.01); *A61M 2037/0007* (2013.01); *A61M 2037/0023* (2013.01); *A61M 2037/0046* (2013.01); *A61M 2037/0053* (2013.01); *A61M 2037/0061* (2013.01); *Y02A 50/387* (2018.01); *Y02A 50/465* (2018.01)

(58) Field of Classification Search
CPC ...... A61M 37/0015; A61M 2037/0023; A61M 2037/0046; A61M 2037/0007; A61M 5/14248; A61M 2037/0061
See application file for complete search history.

(56) References Cited

U.S. PATENT DOCUMENTS

| | | |
|---|---|---|
| 3,221,740 A | 12/1965 | Rosenthal |
| 3,675,766 A | 7/1972 | Rosenthal |

(Continued)

FOREIGN PATENT DOCUMENTS

| | | |
|---|---|---|
| WO | 05/002453 A1 | 1/2005 |
| WO | 05/41871 A2 | 5/2005 |

(Continued)

OTHER PUBLICATIONS

"Flux". Merriam Webster Online Dictionary. <http://www.merriam-webster.com/dictionary/flux>.
(Continued)

*Primary Examiner* — Lauren P Farrar
(74) *Attorney, Agent, or Firm* — Nath, Goldberg & Meyer; Joshua B. Goldberg

(57) ABSTRACT

A system and method of using a high-aspect ratio microdevice for treating, preventing or ameliorating a medical condition is provided.

16 Claims, 4 Drawing Sheets

Related U.S. Application Data

(60) Provisional application No. 60/876,948, filed on Dec. 22, 2006.

(51) Int. Cl.

| | | |
|---|---|---|
| *A61K 9/127* | (2006.01) | |
| *A61K 9/70* | (2006.01) | |
| *A61K 38/21* | (2006.01) | |
| *A61N 1/30* | (2006.01) | |
| *A61K 31/337* | (2006.01) | |
| *A61P 35/00* | (2006.01) | |
| *A61K 31/167* | (2006.01) | |
| *A61K 31/245* | (2006.01) | |

(56) References Cited

U.S. PATENT DOCUMENTS

| | | | |
|---|---|---|---|
| 3,964,482 A | | 6/1976 | Gerstel et al. |
| 4,159,659 A | | 7/1979 | Nightingale |
| 4,222,392 A | | 9/1980 | Brennan |
| 4,286,599 A | | 9/1981 | Hahn et al. |
| 4,340,048 A | | 7/1982 | Eckenhoff |
| 4,381,963 A | | 5/1983 | Goldstein et al. |
| 4,592,753 A | | 6/1986 | Panoz |
| 4,650,484 A | * | 3/1987 | Shaw .................... A61K 31/21 424/448 |
| 4,921,475 A | | 5/1990 | Sibalis |
| 4,938,759 A | | 7/1990 | Enscore et al. |
| 5,139,029 A | | 6/1992 | Fishman et al. |
| 5,156,591 A | | 10/1992 | Gross et al. |
| 5,330,452 A | | 7/1994 | Zook |
| 5,401,242 A | | 3/1995 | Yacowitz |
| 5,527,288 A | | 6/1996 | Gross et al. |
| 5,591,139 A | | 1/1997 | Lin et al. |
| 5,801,057 A | | 9/1998 | Smart et al. |
| 5,843,114 A | | 12/1998 | Jang |
| 5,855,801 A | | 1/1999 | Lin et al. |
| 5,879,326 A | | 3/1999 | Godshall et al. |
| 5,928,207 A | | 7/1999 | Pisano et al. |
| 6,050,988 A | | 4/2000 | Zuck |
| 6,451,240 B1 | | 9/2002 | Sherman et al. |
| 6,503,231 B1 | | 1/2003 | Prausnitz et al. |
| 6,511,463 B1 | | 1/2003 | Wood et al. |
| 6,558,361 B1 | | 5/2003 | Yeshurun et al. |
| 6,603,987 B2 | | 8/2003 | Whitson et al. |
| 6,623,457 B1 | | 9/2003 | Rosenberg |
| 6,743,211 B1 | | 6/2004 | Prausnitz et al. |
| 6,770,480 B1 | | 8/2004 | Cahham |
| 6,815,360 B1 | | 11/2004 | Canham et al. |
| 6,835,184 B1 | | 12/2004 | Sage et al. |
| 6,855,372 B2 | | 2/2005 | Trautman et al. |
| 2002/0095134 A1 | | 7/2002 | Pettis et al. |
| 2002/0138049 A1 | | 9/2002 | Alien et al. |
| 2002/0177839 A1 | | 11/2002 | Cormier et al. |
| 2003/0225362 A1 | * | 12/2003 | Currie .................. A61B 5/0059 604/20 |
| 2003/0225363 A1 | | 12/2003 | Gordon et al. |
| 2004/0060902 A1 | | 4/2004 | Evans et al. |
| 2004/0092498 A1 | | 5/2004 | Blakemore et al. |
| 2004/0181203 A1 | | 9/2004 | Cormier et al. |
| 2004/0199103 A1 | | 10/2004 | Kwon |
| 2004/0241965 A1 | | 12/2004 | Merritt et al. |
| 2005/0000514 A1 | | 1/2005 | Sullivan et al. |
| 2005/0065472 A1 | | 3/2005 | Cindrich et al. |
| 2005/0080028 A1 | | 4/2005 | Catchpole et al. |
| 2005/0085766 A1 | | 4/2005 | Trautman et al. |
| 2005/0096586 A1 | | 5/2005 | Trautman et al. |
| 2005/0096632 A1 | | 5/2005 | Pettis et al. |
| 2005/0261632 A1 | * | 11/2005 | Xu ........................ A61K 9/0021 604/173 |
| 2006/0047242 A1 | * | 3/2006 | Laurent ................ A61B 17/205 604/46 |
| 2006/0264804 A1 | | 11/2006 | Karmon et al. |

FOREIGN PATENT DOCUMENTS

| | | |
|---|---|---|
| WO | 05/044366 A2 | 5/2005 |
| WO | 05/069758 A2 | 8/2005 |
| WO | 05/069758 A3 | 8/2005 |

OTHER PUBLICATIONS

Yang et al., "Topical stratum corneum lipids accelerate barrier repair after tape stripping solvent treatment and some but not all types of detergent treatment", Br. J. Dermatol, Nov. 1995; 133(5):679-85.

Bashir et al., "Physical and physiological effects of stratum corneum tape stripping", Skin Res. Technol. Feb. 2001; 7(1):40-8.

International Search Report of PCT/US2007/088667 published Jul. 3, 2008 as WO 2008/080109 A1.

International Search Report of PCT/UW2006/033877 published May 8, 2008 as WO 2008/054362 A3.

* cited by examiner

MICRODEVICE AND METHOD FOR TRANSDERMAL DELIVERY AND SAMPLING OF ACTIVE SUBSTANCES

CROSS-REFERENCE TO RELATED APPLICATION

This application is a continuation in part application of U.S. patent application Ser. No. 11/961,816, filed on Dec. 20, 2007, which claims benefit of U.S. Provisional Patent Application No. 60/876,948 which was filed on Dec. 22, 2006. The contents of application Ser. No. 11/961,816 and provisional application 60/876,948 are incorporated by reference herein in their entirety.

TECHNICAL FIELD

The present application relates to a microdevice for transdermal delivery of an active substance and methods of using the same.

BACKGROUND

Major reasons for the success of transdermal delivery were the avoidance of first-pass metabolism and ease of use. This increases drug bioavailability in comparison to other delivery methods. Transdermal Drug Delivery Systems (DDS) can also deliver drugs at a steady rate to achieve a sustainable release, which is an additional advantage. However, transdermal drug delivery methods have their drawbacks. Most important is the fact that conventional transdermal system (TTS) technology is only suited for delivering relatively small drugs across the skin. It also suffers from slow onset, because of the outer skin barrier layer, stratum corneum, that limits the through skin drug transport.

New transdermal drug delivery methods are therefore required to drive future growth in transdermal product markets. Biological products would also profit greatly from new, non-invasive delivery technology to replace hypodermic needle injection that is the current standard. The original players in the transdermal field failed to introduce such improvements, which were then introduced by a number of innovator companies.

Broadly speaking, two different new approaches for transdermal drug delivery are currently being pursued: (1) nanoporation/minimum abrasion using a physical device, and (2) nanocarriers using lipid-encapsulated formulation. Sonoporation, thermoporation) use of very fine and short needles belong to the former; ultradeformable carriers (such as Transfersome®, Ethosomes® or fluid liposomes) are examples for the latter. Any of these can deliver small or large molecules across the skin. Some examples of transdermal delivery are described in U.S. Pat. Nos. 7,094,423; 7,049,140; 7,041,870; 7,037,499; 7,034,126; 7,033,598; 7,014,855; 6,991,805; 6,982,084; and 6,979,729.

However, there is a continuing need for an improved, disposable transdermal delivery device for effective delivery of substances in a controlled manner.

SUMMARY

It is an objective of this subject matter to combine both nanocarriers and nanoporation methods to create new transdermal drug delivery vehicles.

It is a further objective of this subject matter to disclose a mechanical applicator to facilitate the application of nanoporation devices.

It is a further objective of this subject matter to disclose a wet device/drug combination method to deliver drug transdermally. The device/drug combination includes, but is not limited to any one or more of the following: (1) pre-treating the mammal using the device, then applying the drug to the mammal; (2) applying the drug to the mammal, then treating the mammal with the device; (3) temporarily anchoring the drug onto the device, then treating the mammal with the device/drug system.

It is a further objective of this subject matter to provide an occlusive layer useful for increasing penetration of an active agent applied to the skin after nanoporation and/or application of the wet formulation.

In some embodiments, the method of delivering an agent described herein includes: (1) applying an applicator to a microdevice to cause the microdevice to contact an area of skin of a mammal (e.g., patient) to generate a prepared area of skin comprising a plurality of nanopores or nanochannels through the stratum corneum in a defined area of skin, (2) applying a wet formulation comprising the agent to the area of skin being prepared either before or after the microdevice has generated the plurality of nanopores or nanochannels in the prepared area of skin, (3) applying an occlusive layer over the agent and directly on the prepared area of skin such that the occlusive layer prevents air from coming into contact with the prepared area of skin following the removal of the applicator and microdevice from the skin, and (4) causing an effective amount of an agent to deliver to the patient through the nanopores or nanochannels in the stratum corneum. The microstructure can be coated with a composition comprising the agent. In some embodiments, the causing is by applying a wet formulation including liposome nanoparticles encapsulating the agent and causing the agent to transport through the stratum corneum into the mammal.

In some embodiments, the present subject matter provides an applicator of the microdevice described herein.

DETAILED DESCRIPTION

Figure 1A:
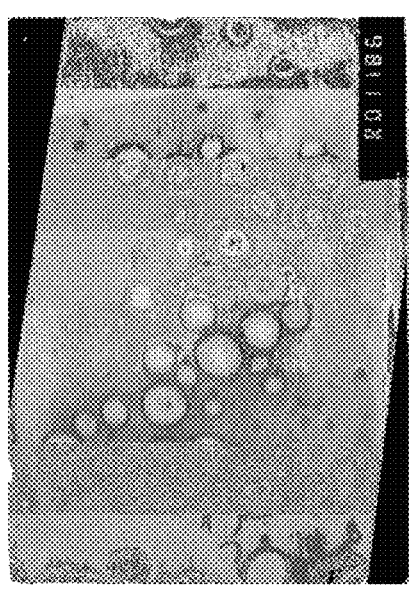
FIGS. 1A and 1B show two preparations of liposome nanoparticles containing docetaxel.

The present subject matter provides high-aspect-ratio microstructures (HARMS) and methods of using the same. The present subject matter also provides methods of using the device for transdermal delivery of drugs, vaccines, diagnostic agents and cosmetic substances and sampling of body fluids for treating, preventing, or ameliorating a medical condition of a mammal such as a human being. In some embodiments, the method comprises treating a topical site of a mammal using a device, and applying an effective amount of an agent to the topical site to allow the agent to penetrate into the body of the mammal. The device can include an array of microstructures. The microstructure can have an aspect ratio of about 5:1, 10:1, 15:1, 20:1 or higher.

In some embodiments, the present subject matter provides a system for topical or systemic delivery of an agent for a medical condition in a mammal (e.g., a patient). The system comprises: (1) a microdevice comprising an array of microstructures, (2) an applicator for applying the microdevice to an area of skin of a patient to generate a prepared area of skin comprising a plurality of nanopores or nanochannels in stratum corneum of the prepared area of skin, and (3) a delivery mechanism for causing the agent to be delivered to the mammal through the nanopores or nanochannels in the stratum corneum of the prepared area of skin. In some embodiments, the microdevice can comprise nanoscale tips and microscale body that can have an aspect ratio of about 5:1, 10:1, 15:1, 20:1 or higher.

In some embodiments, the present subject matter provides a method of delivering an agent for a medical condition to a mammal. The method comprises: (1) applying an applicator to a microdevice to cause the microdevice to contact an area of skin to generate a prepared area of skin comprising a plurality of nanopores or nanochannels through the stratum corneum of the area of skin, (2) applying a composition comprising the agent to the prepared area of skin, (3) applying an occlusive layer over the area of skin, and (4) causing an effective amount of the agent to deliver to the patient through the nanopores or nanochannels in the stratum corneum.

In some embodiments, the method of delivering an agent described herein includes: (1) applying a composition comprising the agent to an area of skin, (2) applying an applicator to a microdevice to cause the microdevice to contact the area of skin to generate a plurality of nanopores or nanochannels through the stratum corneum of the area of skin, (3) applying an occlusive layer over the area of skin, and (4) causing an effective amount of the agent to deliver to the patient through the nanopores or nanochannels in the stratum corneum.

In some embodiments, the method of delivering an agent described herein includes: (1) applying an applicator to a microdevice to cause the microdevice to contact an area of skin of a mammal (e.g., patient) to generate a prepared area of skin comprising a plurality of nanopores or nanochannels through the stratum corneum of the area of skin, (2) applying an occlusive layer over the area of skin, and (3) causing an effective amount of an agent to deliver to the patient through the nanopores or nanochannels in the stratum corneum. The microdevice can be coated with a composition comprising the agent. In some embodiments, the causing is by applying a wet formulation including elastic liposomes comprising liposome nanoparticles encapsulating the agent and causing the agent to transport through the stratum corneum into the mammal. In some embodiments, the wet formulation does not include elastic liposomes.

As used herein, the term "composition" sometimes can be used interchangeably with the term "formulation." The term "wet formulation" refers to any form of wet formulation. In some embodiments, a wet formulation can be a skin patch, cream, ointment, or lotion. In some embodiments, the wet formulation can include elastic liposomes comprising liposome nanoparticles encapsulating an agent. In some embodiments, the wet formulation can include an agent, but not elastic liposomes.

As used herein, the term "agent" refers to any diagnostic, therapeutic, or preventive agents. The term "agent" is sometimes interchangeably referred to as "active agent," "bioactive agent," or "active substance."

Skin Structure

Skin has a biological barrier called stratum corneum in its outer layer. This layer of about 10-25 microns thick prevents most of the molecules from penetrating through the skin. The layer below the stratum corneum is called viable epidermis. Epidermis is between 50 to 100 micron thick. The viable epidermis layer has no blood vessels and the molecules in this layer can be transported to and from the dermis, a layer under the viable epidermis, which is between 1 to 3 mm thick. There are blood vessels, lymphatics and nerves in dermis layer. To date, for example, a skin patch is only able to deliver drug molecules of less than 500 Da. In addition, these small molecules are typically limited to hydrophobic ones.

Requirement of Delivery of Drugs, Vaccines and Cosmetic Substances

Successful transdermal delivery of therapeutic drugs, vaccines and cosmetic substances needs a way to transport molecules, especially large molecules, through the skin barrier, i.e., the stratum corneum. The substance can be delivered into the skin in any form acceptable for pharmaceutical requirements, but a gel composition is preferred to achieve controlled release of the active ingredient(s).

The microdevice described herein can be used for effective transdermal delivery of an agent or a combination of agents. The microdevice can be a microdevice array comprising a plurality of microstructures formed of a metallic, semi-conductor, glass, ceramic, or polymeric material. In some embodiments, the microdevice can be microneedle, microknife, or microblade. In some embodiments, the microdevice comprising microstructures having a nanoscale tip or edge and a microscale body.

Microdevices

The microdevices described herein can be any of microneedles, microblades, microknives, or combinations thereof. As used herein, the term "microneedle" means an elongated element having a ratio of length to largest cross-sectional dimension, of at least about 1:1 or higher. The microneedle may have a regular or irregular cross-sectional shape, such as, for example, circular, elliptical, geometric, or a combination thereof. The needle may optionally include one or more edges running part of or all of the length of the needle's central axis of elongation. The term "microneedle" may also refer to a means that is sufficiently sharp to puncture skin tissue, such as the stratum corneum, to thereby generate nanoconduits.

As used herein, the terms "microblade" and "microknife" both mean an elongated element that is substantially long and thin. For example, having a ratio of length to thickness, of at least about 2:1 or higher. Each microblade includes two surfaces that meet at a single long edge. The length of the edge may be oriented parallel to the skin surface, perpendicular to the skin surface, or at an angle to the skin surface. A microblade with an edge that is significantly parallel to the skin surface may generate a nanoconduit in the skin that is an elongated opening or channel along the surface of the skin that has a narrow width and a depth into the skin as described above for nanoconduits. A microblade with an edge that is significantly perpendicular to the skin surface may generate a nanoconduit in the skin that is an elongated opening in the skin that has a narrow width, or the nanoconduit may have more of a puncture shaped volume wherein the opening has narrow widths in all directions. The terms "microblade" and "microneedle" may also refer to a means having an elongated edge that is sufficiently sharp to puncture skin tissue, such as the stratum corneum, to thereby generate nanoconduits. A microdevice may comprise one or more microneedles, microblades, or microknives.

Aspect-ratio is defined as the ratio of the depth or height of a structure to its lateral dimension. High-aspect-ratio microstructures (HARMS) typically have an aspect ratio higher than about 5:1 and they may be useful for a variety of purposes. In the current subject matter, the tip of microneedle 6 or the edge of the microblade and microknife 6 needs to be sharp in order to lower the insertion force, while the body of microdevice 7 should be high enough to allow it to completely penetrate stratum corneum. A typical size of the needle tip or width of edge on microblades and microknives is smaller than 10 microns, preferably smaller than 5 microns and the height of the microdevices is higher than 20 microns, preferably higher than 50 microns. The aspect ratio of these microdevices, in a preferred embodiment of the current subject matter, are higher than 10:1 with the size of the tip and edge smaller than 5 microns and the height of microdevices higher than 50 microns. HARMS can thus be used to fabricate microdevices including microneedles, microblades, and microknives for drug delivery through skin or body fluids extraction out of skin. Another example of HARMS is nanochannels for microfluidic manipulation and transport. HARMS is typically made by Micro-ElectroMechanical Systems (MEMS) and nanofabrication technology that involves a number of thin film deposition, photolithography, etching and electroplating, injection molding, hot embossing, self-assembly, as well as LIGA process.

A "microneedle array" as used herein refers to a localized arrangement of more than one microneedle, microblade, microknife, or combinations thereof on a surface. The localized arrangement may comprise regular or irregular patterns of the microneedles, microblades, or microknives. For example, microneedles and/or microblades may be arranged in rows, in random formation, or a combination thereof. The microneedle, microblade, microknife, or microneedle array may be present on one or more surfaces of an applicator device.

The microdevice can further include microchannels and microreservoirs. The microdevice or microneedle array may also optionally comprise hollows, voids, non-smooth textures, and/or cavities. One possible use of the hollows, voids, non-smooth textures, and/or cavities is as a site to localize, concentrate, or deliver the agent in embodiments where the agent is to be applied to the skin simultaneously with the generation of the nanoconduits. In some embodiments, the microneedles or microblades comprise hollow channels for delivering an agent via diffusion or active injection, for example from a reservoir. In other embodiments, the microneedles or microblades do not comprise hollow channels for delivering an agent via diffusion or active injection. Some examples of the microdevice are described in U.S. application Ser. No. 10/908,584, filed on May 18, 2005 and Ser. No. 11/510,078, filed on Aug. 25, 2006. The teachings of both applications are incorporated herein in their entirety by reference.

Materials and Device Sterilization

The microdevices can be made of many different materials or their combinations, including metals, ceramics, polymers and glass. Examples of the materials are titanium, stainless steel, nickel, alloy of nickel-iron, silicon, silicon oxide, glass, polymethyl methacrylate (PMMA), polyaryletherketone, nylon, PET, poly(lactic acid), poly(glycolic acid) (PGA), poly(lactic-co-glycolic acid) (PLGA), polycarbonate, and polystyrene. It should have enough mechanical strength to penetrate skin without break and buckle while ensure delivery of drugs, or collect of biological fluids. They can be sterilizable using established protocols (see, for example, moist heat, ethylene oxide or radiation sterilization as stated by ANSI/AAMI/ISO 11134:1993, ANSI/AAMI/ISO 11135:1994 and ANSI/AAMI/ISO 11137:1994, the contents of which are incorporated herein by reference in their entirety).

Elastic Liposome

An elastic liposome is an artificial vesicle designed to be like a cell vesicle, and used to deliver drugs or genetic material into a cell. Its bounding membrane is more flexible than that of a liposome, allowing it to deform and pass through openings in a barrier, such as the skin, whose diameters are much smaller than the average vesicle size. An elastic liposome is an at least bi-component, most often vesicular, aggregate. The main functional characteristic of the aggregate is the extreme flexibility and permeability of its bilayer-like membrane coating. Its basis is the interdependency of local membrane shape and composition, which makes the bilayer self-regulating and self-optimising. The bilayer is thus capable of stress adaptation, via local and reversible bilayer component demixing. All this makes an elastic liposome into a tool suitable for non-invasive and targeted drug delivery, for example across intact skin.

Another beneficial consequence of high bilayer flexibility is the increased elastic liposome affinity to bind and retain water. Ultradeformable elastic liposome vesicles put in a dry environment therefore seek to find water richer region. This forces elastic liposome vesicles applied on open skin to penetrate the skin barrier in a search for adequate hydration. The resulting vesicle migration is a consequence of continuous bilayer adaptation and deformation, but must not compromise unacceptably either the vesicle integrity or the protective skin barrier properties in real-life applications.

A basic elastic liposome is composed of one natural amphiphat (such as phosphatidylcholine) that tends to self-aggregate into vesicles. The latter are then supplemented by at least one bilayer softener (e.g. a biocompatible surfactant). The vesicle-like elastic liposome thus normally possesses an aqueous core surrounded by a complex, very fluid and adaptable lipid bilayer. In its basic organization broadly similar to a simple lipid vesicle (also called liposome), an elastic liposome differs from the latter by its more flexible and permeable, "softened" bilayer membrane. An elastic liposome vesicle can consequently change shape readily and easily by adjusting relative concentration of its two components in the bilayer to the local stress experienced by the complex bilayer. This can be observed indirectly by studying stress- or deformation-dependent vesicle bilayer elasticity or permeability. In a single experiment, the same goal can be achieved by determining the pressure dependency of elastic liposome suspension-flux through a nano-porous filter (with the pores considerably smaller than the average vesicle size). The rate of resulting transport must grow with driving force (head pressure) non-linearly (often sigmoidally) until maximum flow is reached. For an ideal elastic liposome, experiencing no friction in pores, the maximum flow is equivalent to the flux of the suspending liquid measured with a similar trans-filter pressure, and the minimum pressure required to attain good transport is a measure of bilayer flexibility. The observed functional dependency of suspension flux versus pressure can therefore be used to derive bilayer elasticity and flexibility, as well as permeability, based on theoretical description of the underlying enforced transport, viewed as an activated transport process.

Liposome Carrier

In some embodiments, the delivery formulation described herein includes a carrier that comprises elastic liposomes. In some embodiments, the liposomes can be nanoparticles containing lipid-encapsulated therapeutic agents. The liposomes or nanoparticles are complex, most often vesicular, aggregates. In some embodiments, the liposomes or nanoparticles can be optimized to attain flexible and self-regulating membrane, which makes the vesicle very deformable. These liposomes or nanoparticles can be typically applied on the skin and can be engineered to achieve high drug concentration at or near the site of application, diminish local or systemic adverse side effects, and often increase drug potency. The term "high drug concentration" refers to a local concentration enough to achieve desired therapeutic effects without incur significant side-effect.

Liposome nanoparticles can be formed by known method in the art. Generally, the method for forming liposome nanoparticles can be thin film dispersion, reverse-phase evaporation, alcohol infusion, extrusion with or without pressure, which are known in the art (see, e.g.; Planas M. E.; Gonzalez M. E.; Rodriguez L. et al. Noninvasive percutaneous induction of topical analgesia by a new type of drug carrier, and prolongation of local pain insensitivity by anesthetic liposomes. Anesth. Analg 1992. 75(4):615-621; Gregor Cevc, Gabiele Blume, Andreas S, et al. The skin pathway for systemic treatment with patches and lipid based agent carries[J] Advanced Drug Delivery Reviews, 18:349 (1996); Gregor Cevc, et al., Ultradeformable lipid vesicles can penetrate the skin and other semi-permeable barriers unfragmented. Evidence from double label CLSM experiments and direct size measurements Biochimica et Biophysica Acta 1564:21-30 (2002); G. Cevc, et al., Overcoming semi-permeable barriers, such as the skin, with ultradeformable mixed lipid vesicles, Transfersomes® liposomes or mixed lipid micelles. Langmuir, 19:10753-10763 (2003); Gregor Cevc, Lipid vesicles and other colloids as drug carriers on the skin Advanced Drug Delivery Reviews 56:675-711 (2004)).

Figure 1B:
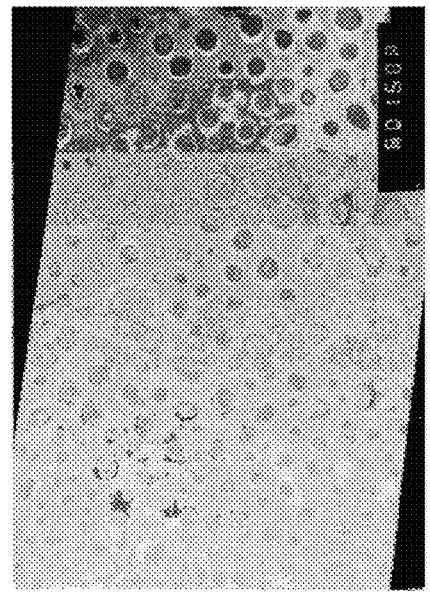

FIGS. 1A and 1B show two preparations of liposome nanoparticles containing docetaxel.

Method of Use

The device described herein can be used for transdermal delivery of an agent or a combination of agents to treat, prevent, or ameliorate a body condition in need of treatment. The method generally includes treating a skin site of delivery with a microdevice described herein, and delivery an agent to the body of a mammal (e.g., a user or patient).

Skin is an elastic tissue that deforms when a force is applied. An applicator and method is described for applying a microneedle/nanoporation device, including a plurality of microneedles with a gentle impact. The method is used to improve transport of an active agent through skin barrier.

It is noteworthy that the prior art uses drug coated tip or hollow microneedles to deliver drug through skin. The present subject matter provides for a method that includes, e.g., pre-treating skin by microneedle array to generate a pre-treated area of skin, and applying to the pre-treated area a wet formulation to allow a therapeutic agent (e.g., drug) or a combination of therapeutic agents to transport through skin. The wet formulation can be in the form of lotion, cream, gel patch, ointment or skin patch. In some embodiments, an occlusive layer is applied over the wet formulation to aid in transporting the therapeutic agents through skin.

In some embodiments, the agent can be included in the microdevice as a coating with or without a carrier. In these embodiments, the agent can be delivered with the microdevice being attached to the site of delivery until a desired quantity or duration of delivery is achieved.

In some embodiments, the agent can be separate from the microdevice. In these embodiments, the skin site chosen for delivery the agent can be pre-treated with the microdevice. The agent can then be applied to the skin site of delivery to allow the agent to penetrate into the body of a user or patient.

The body condition can be a medical condition or a cosmetic condition. Representative medical conditions include, but are not limited to, AIDS, breast cancer, melanoma, liver cancer, lung cancer, blood cancer, pituitary tumors, other cancers, flu, infection, blood disease, cardiac disease, back pain, neck pain, body pain, general pain, arthritis, osteoporosis, headache, depression, smoke, alcoholic, overweight and obesity, menopause, facial hair growth, balding, polycystic ovary syndrome, need of inoculation, need of anesthetics and in particular dermal disease. Representative cosmetic conditions include, but are not limited to, skin aging, skin wrinkle, dark spot, skin discoloration, moisturizing, skin lightening, skin whitening, skin firming, skin lifting, acne, wart, infection, irritation, dry skin and oily skin.

The present microdevices are designed as disposable or re-usable devices. In one embodiment, the microdevices are disposable. Depending on whether the microdevices have coating of active substances on them or not, there are three categories of applications in the delivery of drugs, cosmetic substances and vaccines in the preferred embodiment.

For delivery of a drug, vaccine or cosmetic substance, in one embodiment, the microdevices can be used to perforate or scratch stratum corneum. They are then removed immediately and a formulation of an active substance such as a lotion, cream, gel patch, ointment or skin patch with the active substance is applied to the microdevice treated area right away. The formulation will stay on the skin for a pre-defined period, providing sustainable controlled release of an agent such as a drug, or a combination of agents.

Another embodiment is to store the active agents, as defined below, in the substrate and rely on passive diffusion when the microdevice is in touch with skin.

In yet another embodiment, one can apply the drugs, in the forms of gel, cream, ointment and lotion, or a combination of those forms, to desired treating area on the skin, then treat the skin area with drug using the said microdevice.

In yet a further embodiment, one can pre-coat microneedle shaft with a composition that contains active substances. The coated microneedles are applied to the skin and stay on the skin for the entire period of treatment. The rate of through skin transport can be measured using in vitro or in vivo methods known in the art.

Applicator

In some embodiments, an area of skin can be pre-treated by the microdevice described herein using an applicator. An "applicator device" or "applicator" as used herein refers to a device or object used to generate nanoconduits in the skin. The applicator preferably comprises a driving structure, element, mechanism, and/or means for generating nanoconduits in the skin. The applicator is preferably used in conjunction with a surface, patch, or reservoir comprising an agent to be delivered. The applicator helps to both deliver agent and generate nanoconduits at a single predetermined skin area at a time. Accordingly, in an alternative embodiment, the applicator may simultaneously generate nanoconduits in the skin area and apply a pre-applied agent.

In some embodiments, the applicator may employ vibration of one or more frequencies to create an impact force to generate the nanoconduits. For example, in one embodiment, the applicator may contain an exchangeable head, connecting to a battery-powered motor with two eccentric wheels, transforming rotation to vibration. The vibration can create an impact to the skin through a plurality of microneedles mounted on top of the exchangeable head. The frequency of vibration depends on rotation speed and mass distribution of the eccentric wheels and can be in the range of about 10 Hz to about 50000 Hz. In some embodiments, the frequency range can be between about 1000 and about 8000 Hz. An ordinary artisan can design and make an applicator accordingly. Some examples of designing an applicator for various uses are described in U.S. Pat. Nos. 390,089; 1,512,981; 1,657,312; 1,683,851; 1,780,757; 1,790,962; 1,900,609; 2,411,196; 4,237,911; 4,979,525; 5,054,149; 5,095,924; 5,215,193; 5,328,682; 5,713,492; 5,738,122; D416,387; 6,092,252; and 6,220,253, the contents of which are incorporated herein by reference in their entirety.

In some embodiments, the applicator for mechanical skin treatment comprises:

(a) a housing having a plurality of walls defining an interior space, the interior space having an upper opening permitting selective access to the interior space of the housing, a cover member being removably couplable to the housing such that the cover is for closing the upper opening of the interior space of the housing; and (b) a plurality of microneedle head portion connected to a base portion being removably insertable into the interior space of the housing, each of the applicators being adapted for aiding a user to treat skin;

wherein the plurality of the applicator including a microneedle array assembly comprising:

(i) the microneedle array assembly being adapted for selectively treating skin, (ii) the microneedle assembly having a head portion and a base portion, the head portion being selectively couplable to the base portion such that the base portion is insertable into the interior space of the housing, the base portion of the microneedle array assembly having a pair of depressions, each of the depressions extending along a portion of a length of the base portion, one of the depressions being positioned opposite the other of the depressions such that the depressions are adapted for receiving finger tips of a hand of the user for inhibiting slipping of the base portion from the hand of the user of the applicator.

In some embodiments, the base portion of the applicator described above can further comprises a motor assembly being positioned in the base portion, the head portion having a drive assembly being positioned in the head portion, the drive assembly being operationally coupled to a base portion, the base portion outwardly extending from an upper end of the head portion, the motor assembly being operationally coupled to the drive assembly such that the motor assembly is for actuating the drive assembly, the drive assembly being for oscillating the base portion when the drive assembly is actuated by the motor assembly.

In some embodiments, the applicator described above can further comprise a head portion having a plurality of microneedles extending from the base portion, the microneedles being adapted for treat the skin when the microneedle head portion is oscillated by the drive assembly.

In some embodiments, the applicator described above can further comprise a motor assembly having a motor, the motor having a shaft extending from the motor, the motor being for actuating the shaft, the shaft being for operationally coupling to the drive assembly of the base and head portions such that actuation of the shaft actuates the drive assembly, a power source being operationally coupled to the motor such that the power supply is for providing power to the motor.

In some embodiments, the applicator described above can include a heavy eccentric mass designed to produce vibration upon actuation of the motor, wherein the motor is actuated to bring the base and head portions into vibration so that skin treatment is practiced through the aid of the vibration, the microneedle application method comprising the steps of:

predetermining respective weights of the electric applicator and the heavy eccentric mass as well as an eccentric location of the center of gravity of the heavy eccentric mass; establishing an output of the motor at about 1000-15000 rpm in accordance with the predetermined conditions; producing a vibration of about 1000-15000 rpm by actuating the motor; conducting the vibration to tips of microneedle on the head portion to increase a pressing force acting along an axial direction of the base and head portion by the use of a minute circular ring connecting to the handle part and pressing against skin area need treatment.

In some embodiments, the applicator described above can further include a motor assembly having a switch, the switch being operationally coupled between the power supply and the motor, the switch being for controlling power from the power supply to the motor.

Kits

In another aspect, the present subject matter relates to a kit for delivering an agent to a mammal, comprising:

(a) a microdevice comprising a structure selected from microneedles, microblades, microknives, and combinations thereof;

(b) a wet formulation comprising a bioactive agent;

(c) an occlusive layer; and (d) a mechanism to provide for a driving force sufficient to form nanoconduits on the skin, lined with tissue displaced by the driving force.

In this regard, the driving force can be, but is not limited to, ultrasound, iontophoresis, radio frequency, laser light, heat gradient, or a combination thereof.

In addition, the present kits may further comprises an applicator of the microdevice for applying the microdevice to an area of skin of a mammal; and/or a driving force mechanism for driving the bioactive agent to transport through the stratum corneum of the area of skin into the mammal. The driving force mechanism can comprise ultrasound, radio frequency, heat gradient, laser light, iontophoresis device, or a combination thereof. In a preferred embodiment, the applicator is a mechanical applicator.

The present kits are particularly useful in treating a mammal having a medical condition. Some potential medical conditions treatable by the present kits include, but are not limited to, chronic back pain, a cancer, pre-surgery pain management, operation room pain management, cancer pain, post-surgery pain and lower back pain, and post-surgery pain management.

In this regard, the agent used in the kits can be, but is not limited to, a natural or synthetic vaccine selected from the group consisting of proteins, peptides, paclitaxel, docetaxel, vaccines, protein vaccines, peptide vaccines, gene vaccines, DNA vaccines, and combinations thereof. Further, the vaccine can be against influenza (flu), diphtheria, tetanus, pertussis (DTaP), measles, mumps, rubella (MMR), hepatitis B, polio, *Haemophilus influenzae* type b, chickenpox, tuberculosis, anthrax, yellow fever, rabies, AIDS, cancers, meningococcus, SARS, and/or cholera. In the alternative, the agent is a pain relieving agent. In this regard, the pain relieving agent can be lidocaine, tetracaine, dyclonine, or a combination of thereof.

The formulation used in the present kits can comprise elastic liposomes encapsulating the agent. The elastic liposomes can optionally comprise deformable nanoparticles. In the alternative, the formulation in the present kits does not comprises elastic liposomes. In addition, the formulation can be a topical or systemic delivery formulation selected from a skin patch, cream, ointment, or lotion. In a preferred embodiment, the formulation is a wet skin patch.

Active Agents

In one aspect, active agents or active substances that can be delivered using microdevices are therapeutic agents. The term "therapeutic agent" is used here to refer to active agent that can treat, prevent, and ameliorate a body condition or skin condition that needs treatment. A list of examples includes: drugs, vaccines, peptides, proteins, genes, DNAs, nutraceuticals and cosmetics. The drugs can be administered topically or systemically. Examples of the drugs as active agents include, but not limited to antibiotics, hormones, steroids, anti-inflammatory drugs, protein drugs, DNA drugs whether natural or synthesized, such as Recombinant Erythropoietin (rhEPO), Taxol®, Interferon-alpha-1b, Interferon beta, Interferon gamma, Emla®, Fluorouracil, Lidocaine, Salicylic acid, Pureriran, eflornithine hydrochloride, spironolactone, flutamide, insulin, nanoparticle drugs, Epidural, recombinant human parathyroid hormone, growth hormone, thyroid, cortisol, estrogen, progesterone, and testosterone. Examples of vaccines active agents include, but not limited to: vaccine against influenza (flu), diphtheria, tetanus, pertussis (DTaP), measles, mumps, rubella (MMR), hepatitis B, polio, *Haemophilus influenzae* type b, chickenpox, tuberculosis, anthrax, yellow fever, rabies, AIDS, cancers, meningococcus, SARS and cholera. More examples of cosmetic substances as active agents include, but not limited to: botulinum toxin type A, hyaluronic acid and its derivatives, acetyl hexapeptide-3, vitamin A, vitamin C, vitamin E, alpha-hydroxyacids, collagen and hormones. Diagnostic reagents are also included. Examples include, but not limited to, quantum dots, functionalized nanoparticles, magnetic particles for diagnostic purpose.

The dosage of the agent can vary according to the medical conditions. The effective amount of an agent that has been well established in the art can be publicly available. Such information can be obtained from the U.S. Food and Drug Administration (FDA), e.g., FDA website. For example, LidoDerm® publishes this type of information.

In some embodiments, the agent is a pain relieving drug for neuropathic or nociceptive pain management. Such pain relieving drug includes, but is not limited to, Lidocaine; Prilocaine, Tetracaine, Ibuprofen; Acetaminophen; Capsaicin; EMLA®; Tramadol (Ultram); Gabapentin, Tramadol hydrochloride, Corticosteroids, Sufentanil, Clonidine, Bupivacaine, Tricyclic antidepressants, opioid analgesics such as morphine, Hydromorphone, naloxone (Narcan), Talwin, Nubain, Stadol, Fentanyl, Meperidine, Hydrocodone, Codeine, Oxycodone; non-selective NSAIDs such as Celecoxib (Celebrex), rofecoxib (Vioxx), valdecoxib (Bextra); or combinations thereof. In some embodiments, the pain relieving drug described herein can specifically include any of the drug/agents listed herein.

In some embodiment, the active agent can be muscle relaxants, which include, but are but not limited to, Benzodiazepines; Methocarbamol; Carisoprodol; Chlorzoxazone; Metaxalone; Cyclobenzaprine, or combinations thereof. In some embodiments, the muscle relaxants described herein can specifically exclude any of the drug/agents listed herein.

Drug Delivery

In one aspect, the present subject matter provides a device 10 for delivery of therapeutic active agent as defined above across the skin barrier, stratum corneum layer. Once the substances pass the stratum corneum, there is less resistance for the substances to diffuse into the subsequent layers of the skin: epidermis and dermis. The substances will be absorbed by micro blood vessels and lymphatics in the dermis layer and delivered to entire human body. Microdevices disclosed in the current subject matter can enhance through skin penetration of molecules of molecular weight lower than 500 Dalton. In some embodiments, microdevices can also enable through skin transport of large molecules of molecular weight higher than 500 Dalton. The molecular weight of Bovine Serum Albumin is 66,000 Dalton. The molecular weight of Botulinum Toxin Type A is 150,000 Dalton and the molecular weight of Interferon-Alpha-1b is 17,000 Dalton.

In this regard, the present systems permit the agent to permeate the skin at least 10 times faster than in a system where the formulation is applied to an area of skin which does not contain any generated nanoconduits. In this regard, the agent can permeate the skin to cumulative amounts at least 10 times higher than in a system where the formulation is applied to an area of skin which does not contain any generated nanoconduits.

In some embodiments, the drug delivery of the present subject matter can be achieved by preparing an area of skin to generate a prepared area of skin and then applying an agent or drug to the prepared area of skin to allow a pre-defined amount of the drug or agent to pass through the stratum corneum of the prepared area of skin.

In some embodiments, the prepared area of skin can be prepared using a device, e.g., a spring-powered mechanical applicator to apply microneedles to an area of skin. The mechanical applicator can be any structure or design and can cause a mechanical force to be applied to the microneedle against the area of skin to generate pores or channels in the stratum corneum in the area of skin in a pre-defined size and depth. The size and depth of the pores or channels can facilitate the release of controlled amount of an agent or drug through skin.

In some embodiments, the prepared area of skin can be further treated using an ultrasound device or a mechanical vibrator to apply microneedles to an area of skin. The ultrasound device or mechanical vibrator can cause a pre-set mechanical force to be applied to the microneedle against the area of skin to generate pores or channels in the stratum corneum in the area of skin in a pre-determined size and depth. The size and depth of the pores or channels can provide for controlling the amount of an agent or drug of delivery. It is noteworthy that the ultrasound device or mechanical vibrator can be an effective way to perforate an elastic skin tissue to generate pores or channels in a pre-defined size and/or depth.

In some embodiments, the prepared area of skin can be prepared in a pre-defined size or dimension (e.g., a dimension of 1 cm.times.1 cm) using an array of microknives or microblades by slicing or lacerating the stratum corneum in an area of skin to generate nanochannels in a pre-defined depth and/or dimension. The dimension and/or depth of the laceration and the dimension of the prepared area of skin can provide for controlling the amount of an agent or drug.

Allowing an agent or drug to pass through the stratum corneum of a prepared area of skin can be achieved by a variety of mechanisms. For example, the allowing can be achieved by diffusion of the agent or drug from a topical composition (e.g., a formulation such as lotion, cream, gel patch, ointment or skin patch) into the body of a patient or user via the prepared area of skin. In some embodiments, the allowing can be achieved by a driving mechanism, for example, iontophoresis, sonophoresis, radiofrequency (RF) or heat or a combination of these to actively drive agents through the skin.

Iontophoresis, sonophoresis, radiofrequency (RF) or heat are well developed mechanisms for promoting or enhancing drug delivery. Some examples of iontophoresis systems in drug delivery are described in websites online. Some examples of sonophoresis systems in drug delivery are described in Becker B, Helfrich S, Baker E, et al. Ultrasound with topical anesthetic rapidly decreases pain of intravenous cannulation. Academic Emergency Medicine 2005; 12:289-295; Katz N, Shapiro D, Herrmann T, et al., Rapid onset of cutaneous anesthesia with EMLA cream after pretreatment with a new ultrasound-emitting device. Pain Trials Center, Brigham and Women's Hospital, Boston, Mass.; Mitragotri S, Kost J, Low frequency sonophoresis: A Review. Advanced Drug Delivery Reviews 2004; 56:589-601.

Topical or Systemic Delivery of Cosmetic Substances

It is known to one in the art that certain substances have specific functions as cosmetics. For example, Botulinum Toxin Type A is a toxin that blocks neuromuscular transmission when it is injected in small amounts (e.g., 10 units per 0.1 ml injection volume) into specific muscles to treat and reduce wrinkles on the face. The maximum dosage recommended as a single injection for any one muscle at any one spot is 25 units. If overdosed or the injection is incorrectly performed, the patient can be left with an immobile face or droopy eyelids till the effect of the injection wears off. The side effects include numbness, swelling and headaches. Administered through microdevices disclosed in the current subject matter, it is possible to provide a controlled release of Botulinum Toxin Type A and keep an optimal local concentration to achieve the best result while minimizing the side effects. In a preferred embodiment of this subject matter, gel patch with botulinum toxin type A is applied to the skin pre-treated with microneedle array. No through skin transport was observed without application of microdevices while significant through skin transport of botulinum toxin type A was observed using the said microdevice. More examples were provided in the above "active agents" section.

Transdermal delivery of an agent through skin treated by the microdevice described herein has less dependency on molecular weight of the agent. Using the methods described herein, practically, any cosmetic substances can be delivered using microdevices herein. Local concentration can be adjusted through loading and composition for controlled release, as well as a combination of microneedle height, density, size and shape. In one embodiment of this subject matter, one can deliver hyaluronic acid gel through diffusion enhanced by microdevices. Hyaluronic acid is a substance that exists naturally in the body. A major important function of hyaluronic acid is to carry and bind water molecules. Stabilized non-animal hyaluronic acid does not contain animal protein and does not require a skin test prior to treatment. It is thus a preferred embodiment of this subject matter to use microdevices to delivery locally stabilized non-animal hyaluronic acid to treat wrinkles and facial lines.

Yet, in a further embodiment of this subject matter, one can locally delivery collagen by microneedles, e.g., for allergic skin test and controlled release of collagen into the skin.

Yet, another embodiment of this subject matter is to provide for local delivery of acetyl hexapeptide-3. This molecule is a non-toxic, non-irritant compound that modulates the excessive stimulation of the facial muscles, relaxing facial tension and it can reduce and prevent the formation of new wrinkles due to over-stimulation of facial muscles. More examples include but not limited to: vitamin A, vitamin C, vitamin E, alpha-hydroxyacids, hormones, or combinations thereof.

Delivery of Vaccines

In some embodiments, the microdevice provided herein can be used for topical or systemic delivery of vaccines below the stratum corneum layer. The type of vaccines includes conventional vaccines as well as protein, peptide, DNA vaccines and the like as previously described. Vaccination can be performed by treating a skin site with the microdevice and then delivering a vaccine composition to a user.

Delivery of Large Molecules

In some embodiments, the microdevice provided herein can be used for topical or systemic delivery of drug with large molecules. The drug can be a protein or peptide. In some embodiments, the drug can be a chemical drug with a relatively high molecular weight. As used herein, the term large molecule refers to a drug having a molecular weight higher than about 300 Daltons. For example, the molecule can have molecular weight higher than about 500 Daltons, higher than about 1000 Daltons, higher than about 5,000 Daltons, higher than about 10,000 Daltons, higher than about 20,000 Daltons, higher than about 50,000 Daltons, higher than about 100,000 Daltons, higher than about 200,000 Daltons, higher than about 500,000 Daltons, or higher than about 1,000,000 Daltons.

In some embodiments, the drug can be paclitaxel, docetaxel, insulin, Recombinant Erythropoietin (rhEPO), Interferon-alpha, Interferon beta, Interferon gamma, nanoparticle drugs, recombinant human parathyroid hormone, growth hormone, thyroid, cortisol, estrogen, progesterone, and testosterone. Examples of vaccines active agents include, but not limited to: vaccine against influenza (flu), diphtheria, tetanus, pertussis (DTaP), measles, mumps, rubella (MMR), hepatitis B, polio, *Haemophilus influenzae* type b, chickenpox, tuberculosis, anthrax, yellow fever, rabies, AIDS, cancers, meningococcus, SARS and cholera. Examples of cosmetic substances as active agents include, but not limited to: botulinum toxin type A, hyaluronic acid and its derivatives, acetyl hexapeptide-3, vitamin A, vitamin C, vitamin E, alpha-hydroxyacids, collagen and hormones. Diagnostic reagents are also included. Examples include, but not limited to, quantum dots, functionalized nanoparticles, magnetic particles for diagnostic purpose.

Pain Management

In some embodiments, the microdevice described herein can be used for pain management. The microdevice can be used to facilitate transdermal delivery of a pain relieving agent or a combination of them so as to treat, reduce or prevent pain. In some embodiments, a skin site can be treated with the microdevice and then a pain relieving agent or drug composition can be applied to the treated site, allowing transdermal delivery of these agents to a user.

The pain relieving agent can be any pain relieving agent approved by FDA or used in medical practice elsewhere in the world. In some embodiments, the pain relieving drug can be, but are not limited to, NSAIDs, COX-2 inhibitors, steroids, muscle relaxants. Specifically, such as Lidocaine; Prilocaine, Tetracaine, Ibuprofen; Acetaminophen; Capsaicin; EMLA®; Tramadol (Ultram); Gabapentin, Tramadol hydrochloride, Corticosteroids, Sufentanil, Clonidine, Bupivacaine, Tricyclic antidepressants, opioid analgesics such as morphine, Hydromorphone, naloxone (Narcan), Talwin, Nubain, Stadol, Fentanyl, Meperidine, Hydrocodone, Codeine, Oxycodone; non-selective NSAIDs such as Celecoxib (Celebrex), rofecoxib (Vioxx), valdecoxib (Bextra); or combinations thereof. In some embodiments, the pain relieving drug described herein can specifically exclude any of the drug/agents listed herein.

The pain management can be carried out according to a management regime prescribed by a treating doctor. For example, in some embodiment, the pain management is chronic or acute pain management. The pain management regime can be but not limited to, lower back pain, post-herpetic neuralgia, cancer pain, diabetic neuropathy, phantom limb pain, spinal stenosis/sciatica, spinal mets, HIV pain, post-surgery pain, pre-surgery preparation, operation room pain management, pain caused invasive medical procedures such as needle injection, cannulation.

Different from prior art, the current subject matter involves topical or systemic delivery of pain relieve agent to deep tissues through assistance of a combination of active transdermal delivery methods such as sonophoresis, iontophoresis, laser ablation, radio frequency or heat treatment after the startum corneum are treated with the said microdevices.

In another aspect, the present systems and methods are useful for treating cancer.

Controlled Release

The microdevices herein preferably deliver drug molecules through skin at a rate that is sufficient to maintain a therapeutic useful concentration in plasma. The size, density, shape and length of the microdevices can be adjusted to meet the delivery requirement. The microdevices can be further coated with a composition that contains active therapeutic molecules, or vaccines, or cosmetic substances, together with polymer binders such as chitosan, carbopol 934P, cellulose and starch to form a dry film. Additional additives of binders, rheology modifiers, surface active agents, stabilizer, rehydration agents may be used. The special composition can control the dissolve rate of the active drug molecule and regulate the drug release rate. The microdevices may be integrated with embedded microfluidic channels that connect to microreservoirs.

In this regard, the present the methods result in a plateau plasma concentration of agent, wherein the plateau is preferably maintained within 80% of the peak concentration from 10 hours after first contact and up to at least 24 hours after first contact. The plateau can be maintained within 80% of the peak concentration from 10 hours after first contact and up to at least 48 hours after first contact.

Accordingly, the agents herein have a "drug permeation", meaning as the amount of agent (mg, or mmol) diffused across the skin barrier within a defined time.

Occlusive Layer

In some embodiments, the method of delivering an agent, or a combination of agents may include applying an occlusive layer. The occlusive layer may be applied over the applied agent and directly on the prepared area of skin, or the area of skin, such that the occlusive layer prevents air from coming into contact with the prepared area of skin following the removal of the applicator and microdevice from the skin. The occlusive layer is advantageous for preventing evaporation of the agent or combination of agents, and most importantly, allows for increased penetration of an active agent across the skin. The occlusive layer is useful for preventing evaporation of the wet formulation and provides increased penetration of the active agent across the skin.

In some embodiments, an occlusive layer is applied directly on the prepared area of the skin such that the occlusive layer prevents air from coming into contact with the prepared area of skin following the removal of the applicator and microdevice. The prepared area of skin is generated by applying the applicator to an area of the skin, and subsequently, the occlusive layer is applied directly on the abraded area of skin, either with or without a wet formulation. The occlusive layer may be placed directly on the prepared area of skin to prevent air or other fluids from entering the abraded skin area, other than the et formulation comprising the agent. In some embodiments, in order to prevent air from contacting the prepared area of skin, the occlusive layer must contact the entire abraded area.

Figure 2:
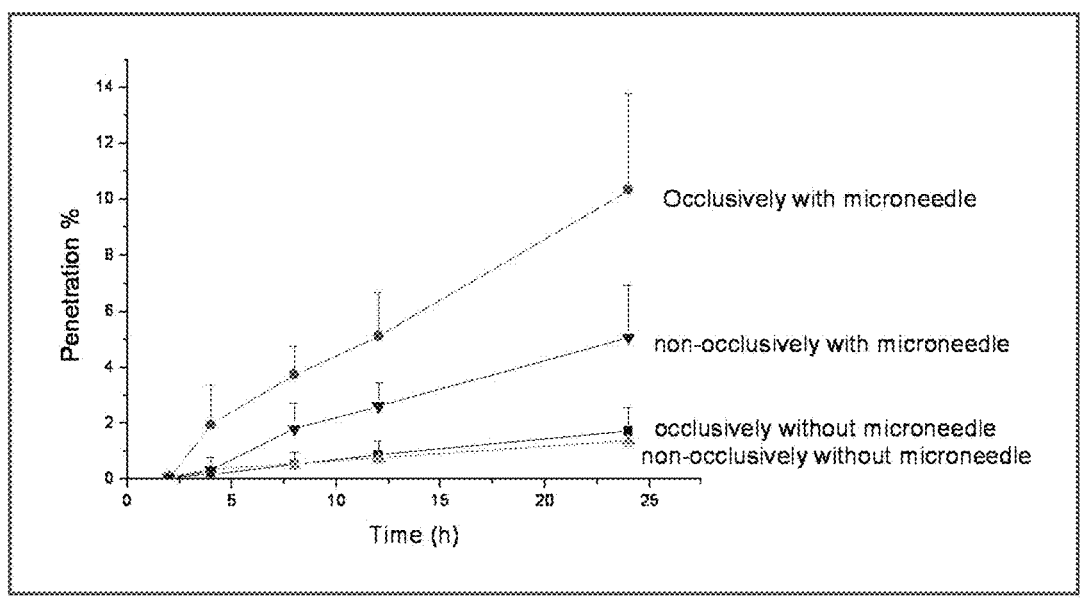
FIG. 2 shows penetration (%) of docetaxel in elastic liposomes with or without microneedle and with or without an occlusive layer.
Figure 3:
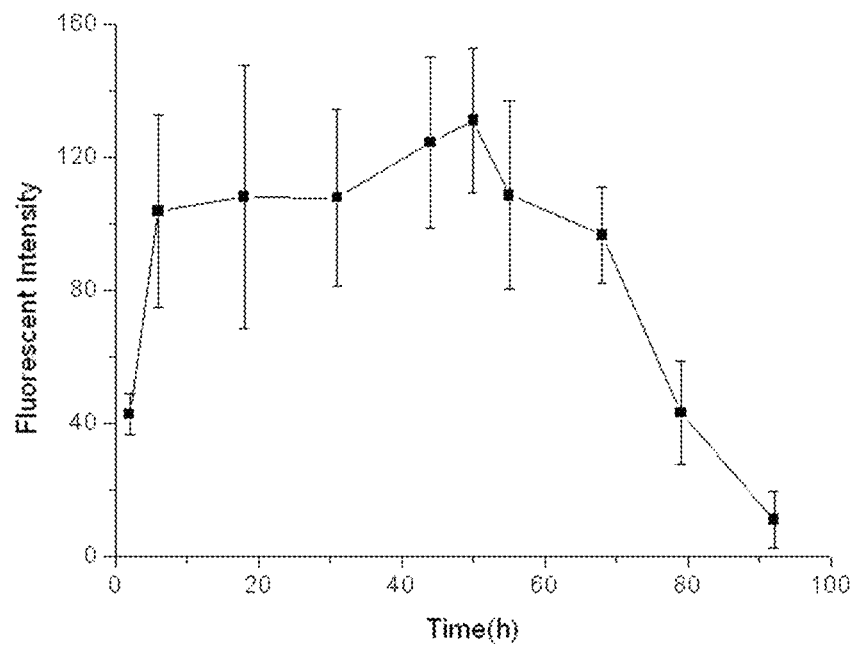
FIG. 3 shows fluorescence labeled docetaxel encapsulated within elastic liposome nanoparticles being successfully transported through skin.

Applying the occlusive layer after applying a wet formulation comprising the agent to the prepared area of skin after the microdevice has generated the plurality of nanopores or nanochannels in the prepared area of skin substantially increases the rate of penetration of the agent. In fact, as described in more detail below, FIG. 2 shows the difference for drug delivery between occlusive and non-occlusive treatment following microneedle pre-treatment. From the data shown in FIG. 2, it is clearly evident that applying an occlusive layer after microneedle pre-treatment significantly improves drug delivery since the rate of penetration increases. When compared to non-occlusive treatment after microneedle pre-treatment, or even non-occlusive pretreatment with no microneedle pre-treatment, the rate of penetration is substantially less. In fact, the drug delivery data shown in FIG. 3 shows that the present method unexpectedly provides 72 hours of extended drug release.

In this regard, the data from the graph shown in FIG. 2 is provided in the Table 1, which shows the effect of the occlusive layer on penetration.

TABLE 1

| Time (h) | Occlusively with microneedles | Standard Deviation | Non-occlusively with microneedles | Standard Deviation | Occlusively without microneedles | Standard Deviation | Non-occlusively without microneedles | Standard Deviation |
|---|---|---|---|---|---|---|---|---|
| 2  | 0.07  | 0.07 | 0.08 | 0.08 | 0.06 | 0.09 | 0.11 | 0.06 |
| 4  | 1.94  | 1.41 | 0.32 | 0.46 | 0.18 | 0.11 | 0.35 | 0.30 |
| 8  | 3.74  | 1.02 | 1.80 | 0.91 | 0.54 | 0.42 | 0.54 | 0.16 |
| 12 | 5.13  | 1.55 | 2.60 | 0.85 | 0.88 | 0.49 | 0.76 | 0.16 |
| 24 | 10.33 | 3.43 | 5.07 | 1.88 | 1.71 | 0.83 | 1.40 | 0.22 |

The data in Table 1 shows comparative data of the percent penetration of an active agent (docetaxel) in elastic liposomes across skin under four different sets of conditions, where the active is applied to the skin with or without microneedle preparation of skin or use of an occlusive layer:
 (1) yes microneedle, yes occlusive layer;
 (2) yes microneedle, no occlusive layer;
 (3) no microneedle, yes occlusive layer; and
 (4) no microneedle, no occlusive layer.

The data in Table 1 shows that adding an occlusive layer does not change the percent penetration over 24 hours of the agent across skin not prepared with microneedles. The two data sets ("occlusively without microneedles" vs. "non-occlusively without microneedles") show statistically the same amount of penetration. In other words, the evidence shows that adding an occlusive layer does not increase the penetration of the agent across unprepared skin.

Further, FIG. 2 shows that adding an occlusive layer to skin prepared with microneedles unexpectedly and significantly increases the percent penetration of the active across the prepared skin. This unexpected increase in penetration is due to the combination of the presence of microneedle prepared skin and adding an occlusive layer to the microneedle prepared skin.

Figure 6:
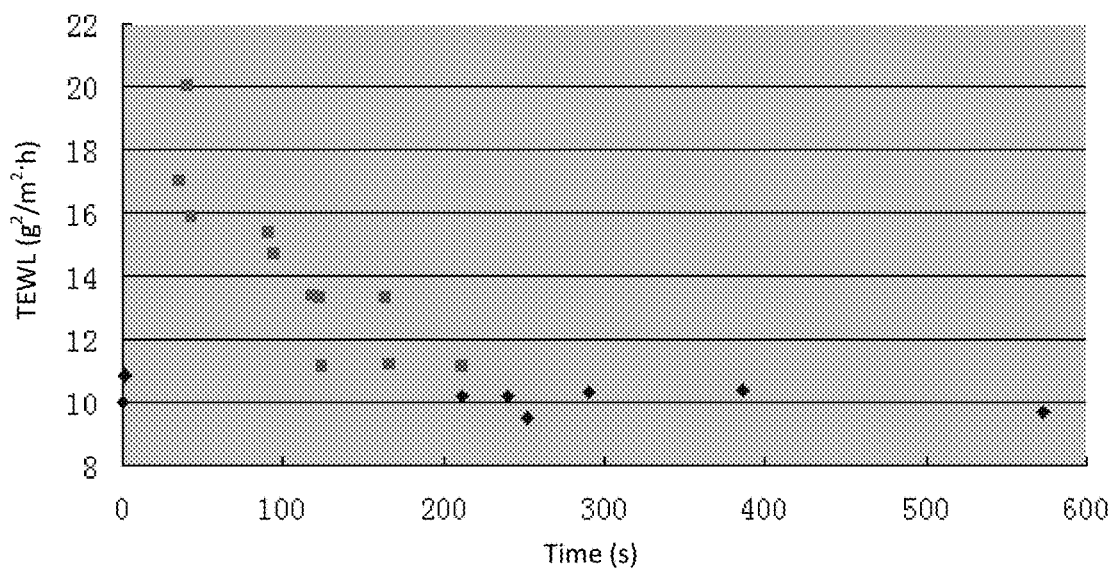
FIG. 6 shows a graph of Trans-Epidermal Water Loss with or without microneedle application.

FIG. 6 shows a graph of Trans-Epidermal Water Loss with or without microneedle application. In the graph, the X-axis represents the time in seconds and the Y-axis represents the Trans-Epidermal Water Loss (TEWL). The diamond shaped data points represent the TEWL baseline, and the square shaped data points represent the increase of TEWL after the treatment with the present microdevice. The curve of the square shaped data points decreases over time and eventually merges with the diamond shaped data points at about 200 seconds. This indicates that the skin barrier was initially compromised and penetrated by the microdevice and the skin quickly recovers in about 120-200 seconds or 20-30 minutes.

Figure 7:
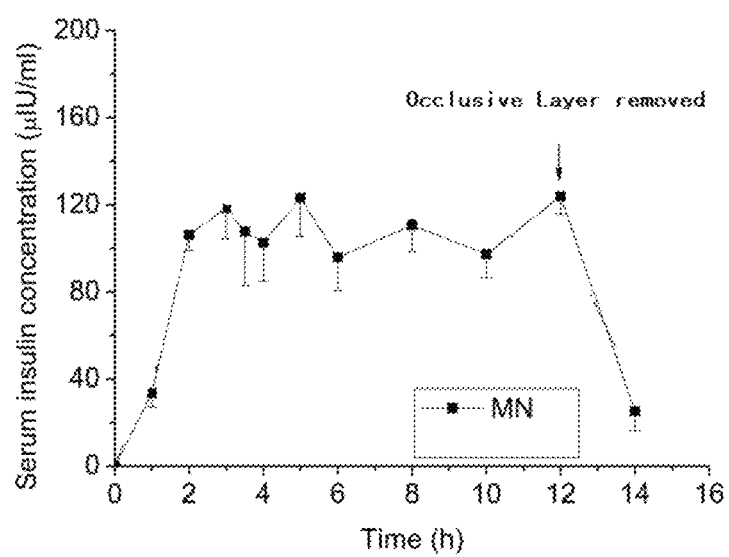
FIG. 7 shows a graph of serum insulation concentration with an occlusive layer applied.

FIG. 7 shows a graph of serum insulation concentration with an occlusive layer applied. In particular, the graph shows the prolife of Novolin R® serum insulin concentration vs. time in a diabetic rat after the administration of insulin by the present microdevice. The serum concentration reached 110±5.37 μIU/ml and stayed relatively constant at this level when the occlusive layer was applied. This indicates that the delivery channels were kept open to meet the basal insulin delivery need. The serum concentration rapidly dropped after the removal of the occlusive layer, indicating that the pores closed and the insulin delivery source was cut off.

Before the filing of this application, it was generally considered that the skin barrier rapidly restores resulting in a shorter period of drug delivery. For example, Yang et al., "Topical stratum corneum lipids accelerate barrier repair after tape stripping, solvent treatment and some but not all types of detergent treatment", Br. J. Dermatol, 1995 November; 133(5):679-85 (hereinafter "Yang") and Bashir et al., "Physical and physiological effects of stratum corneum tape stripping", Skin Res. Technol. 2001 February; 7(1):40-8 (hereinafter "Bashir"), teach various means of disrupting the barrier function of the strateum corneum (SC) have been extensively described, including tape-stripping and acetone treatment. Specifically, tape stripping removes the SC mechanically, while acetone treatment extracts lipids from the SC. Restoration of barrier function occurs in a similar amount of time following tape stripping and acetone treatment. Notwithstanding the type of method for penetrating the skin, the pores of the skin generally stay open for a very short period of time providing a limited window for drug delivery. The present microdevice and method overcomes these deficiencies. The present subject matter significantly improves drug delivery since the rate of penetration increases and allows extended drug delivery, i.e., 72 hours as shown in FIG. 3.

The Integrated Sensors

It is another aspect of the subject matter to provide a device in which clinical biosensor and/or sensor arrays are fabricated in the close vicinity of these HARMS structures. For example, microneedle can collect an extremely low sample volume of body fluids from a patient and allow rapid point-of-care analysis of body fluids. In one embodiment, the sample volume extracted is below 0.1 microliter, typically around 0.01 microliter.

Methods for HARMS Fabrication

The HARMS were fabricated using MEMS (Micro-Electro-Mechanical Systems) microfabrication technology. The typical fabrication process involved lithography, wet etch and dry etch, thin film deposition and growth, electroplating, as well as injection molding and hot embossing. One example of fabrication method was to use Bosch process that allowed deep Si etch. It formed HARMS suitable either as device body or mold for further processing. The aspect ratio was higher than 5:1, independent to feature size and pattern shape as long as the features can be defined by lithography. Another fabrication method was KOH or TMAH wet etch of single crystal Si substrate that is <100> orientation or <110> orientation. Yet another fabrication method was using HF solution to electrochemically form porous Si structures. Metals was used for the fabrication of HARMS through a maskless process called electropolishing starting from a structure fabricated by traditional machining methods such as cutting, electro-discharge machining, milling, grinding, polishing and drilling. Use of any single method herein or a combination of these methods as further disclosed in the examples below led to the form of desired HARMS disclosed in the current subject matter.

EXAMPLES

Example 1. Delivery of Docetaxel with Combination of Microneedle with Flexible Liposome Nanoparticles FIGS. 2 and 3 showed the efficacy of transdermal delivery of agents of the present subject matter. In the test shown in FIGS. 2 and 3, an area of skin was pre-treated with the microneedles described above. Then a formulation of a fluorescence labeled albumin (molecular weight is 66,000) was applied and successfully transport them through skin (FIG. 3). The pore formed by the microneedles will not completely be closed within 72 hours after application of the microneedles. FIG. 2 shows Penetration (%) of docetaxel in elastic liposomes with or without microneedle.

Example 2. Delivery of Interferon with Combination of Microneedle

Figure 4:
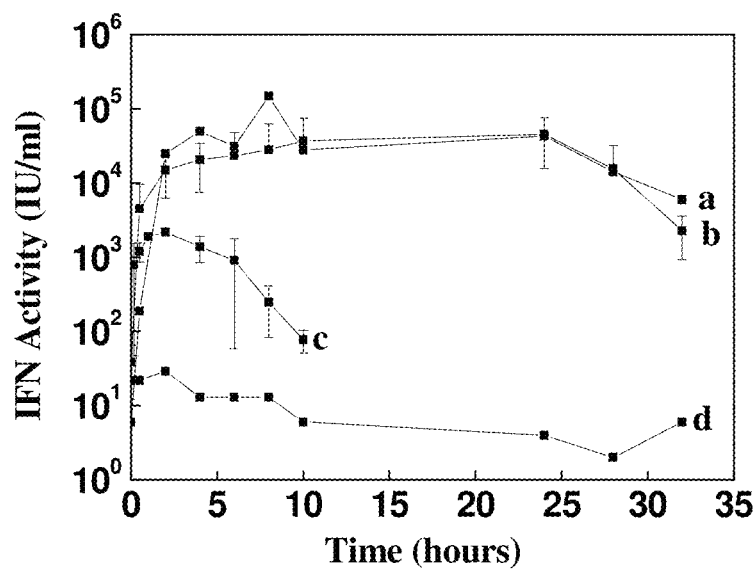
FIG. 4 shows delivery of interferon via different methods.

FIG. 4 shows delivery of interferon via different methods. The effectiveness of various delivery methods was assessed by measurement of interferon activity: (a) microneedle with a wet interferon gel on the microneedles, (b) microneedle with a wet interferon gel patch on skin pre-treated with microneedles, (c) subcutaneous injection, and (d) wet interferon gel without microneedle as control sample.

Figure 5:
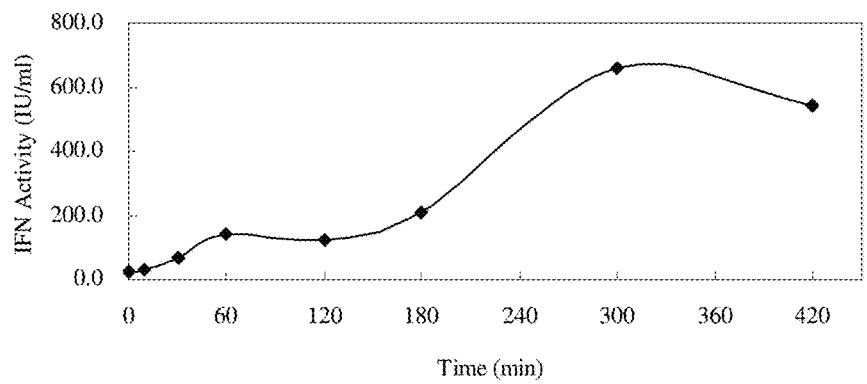
FIG. 5 shows delivery of interferon with a dry formulation.

FIG. 5 shows delivery of interferon with a dry formulation. As FIG. 5 shows, when the patch is dried, the delivery rate dropped dramatically.

In sum, FIGS. 4 and 5 show that delivery of interferon using a dry patch is less effective as it is using a wet patch.

While particular embodiments of the present subject matter have been shown and described, it will be obvious to those skilled in the art that changes and modifications can be made without departing from this subject matter in its broader aspects. Therefore, the appended claims are to encompass within their scope all such changes and modifications as fall within the true spirit and scope of this subject matter.

I claim:

1. A method of delivering an agent, or a combination of agents, for a medical condition to a mammal, comprising
    applying an applicator comprising a microdevice to cause the microdevice to contact an area of skin of the mammal to generate a prepared area of skin comprising a plurality of nanopores or nanochannels through the stratum corneum of the prepared area of skin and removing the applicator and microdevice from the skin immediately after the microdevice has penetrated the skin,
    applying a wet formulation comprising the agent to the area of skin being prepared either before or after the microdevice has generated the plurality of nanopores or nanochannels in the prepared area of skin,
    subsequently applying an occlusive layer over the agent and directly on the prepared area of skin such that a lower surface of the occlusive layer only contacts the wet formulation or the skin so the occlusive layer prevents air from coming into contact with the prepared area of skin following the removal of the applicator and microdevice from the skin, and
causing an effective amount of agent to deliver to the patient through the nanopores or nanochannels in the stratum corneum at a rate percent penetration that is higher than the rate of percent penetration if no nanopores or nanochannels are present.

2. The method of claim 1, wherein causing an effective amount of the agent to deliver to the patient comprises:
    allowing the agent to diffuse into the patient from the formulation, or
    driving the agent into the patient by applying a driving force to the formulation.

3. The method of claim 2, wherein the driving force is selected from iontophoresis, sonophoresis, radiofrequency (RF), heat gradient or a combination of these.

4. The method of claim 1, wherein agent is encapsulated within elastic liposomes.

5. The method of claim 4, wherein the elastic liposome comprises liposome nanoparticles.

6. The method of claim 1, wherein the wet formulation does not comprise elastic liposomes.

7. The method of claim 1, wherein the mammal has a medical condition,
    wherein the agent is a natural or synthetic vaccine selected from the group consisting of proteins, peptides, paclitaxel, docetaxel, vaccines, protein vaccines, peptide vaccines, gene vaccines and DNA vaccines, and
    wherein the vaccine is against influenza (flu), diphtheria, tetanus, pertussis (DTaP), measles, mumps, rubella (MMR), hepatitis B, polio, *Haemophilus influenzae* type b, chickenpox, tuberculosis, anthrax, yellow fever, rabies, meningococcus, and cholera.

8. The method of claim 1, wherein the agent is a pain relieving agent.

9. The method of claim 8, wherein the medical condition is chronic back pain.

10. The method of claim 8, wherein the medical condition is a cancer.

11. The method of claim 8, wherein the medical condition is pre-surgery pain management, operation room pain management or post-surgery pain management.

12. The method of claim 8, wherein the pain relieving agent is lidocaine, tetracaine, dyclonine or a combination thereof, and
    wherein the formulation is a topical or systemic delivery formulation selected from lotion, cream, gel patch, ointment or skin patch comprising lidocaine, tetracaine, dyclonine or a combination thereof.

13. The method of claim 8, wherein the applicator is a mechanical applicator.

14. The method of claim 1, wherein the formulation is a topical or systemic delivery formulation selected from a skin patch, cream, ointment, or lotion.

15. The method of claim 14, wherein the mammal is a human and wherein the medical condition is cancer pain, post-surgery pain and lower back pain.

16. The method of claim 1, wherein the formulation is a wet skin patch.

* * * * *